United States Patent
Coussot et al.

(10) Patent No.: US 9,546,999 B2
(45) Date of Patent: Jan. 17, 2017

(54) METHOD FOR DETECTING AND QUANTIFYING A MOLECULE INCLUDING AT LEAST ONE PROTONATED GROUP ON A SOLID SUBSTRATE

(75) Inventors: Gaëlle Coussot, Lunel (FR); Odile Vandenabeele-Trambouze, Locmelar (FR); Isabelle Desvignes, Juvignac (FR); Michel Dobrijevic, Floirac (FR); Aurélie Le Postollec, Floirac (FR); Pascale Chazalnoel, Dremil-Lafage (FR)

(73) Assignee: 1/ CENTRE NATIONAL D'ETUDES SPATIALES, Paris (FR)

( * ) Notice: Subject to any disclaimer, the term of this patent is extended or adjusted under 35 U.S.C. 154(b) by 385 days.

(21) Appl. No.: 12/920,460

(22) PCT Filed: Mar. 5, 2009

(86) PCT No.: PCT/EP2009/052637
§ 371 (c)(1),
(2), (4) Date: Nov. 22, 2010

(87) PCT Pub. No.: WO2009/112430
PCT Pub. Date: Sep. 17, 2009

(65) Prior Publication Data
US 2011/0098194 A1    Apr. 28, 2011

(30) Foreign Application Priority Data
Mar. 5, 2008  (FR) ...................................... 08 51425

(51) Int. Cl.
*G01N 33/52*     (2006.01)
*G01N 33/68*     (2006.01)
*G01J 3/12*      (2006.01)

(52) U.S. Cl.
CPC .......... *G01N 33/52* (2013.01); *G01N 33/6803* (2013.01)

(58) Field of Classification Search
CPC ............................. G01N 33/52; G01N 33/6803
See application file for complete search history.

(56) References Cited

U.S. PATENT DOCUMENTS

| | | | |
|---|---|---|---|
| 5,705,649 A * | 1/1998 | Shultz et al. ................. | 548/126 |
| 6,555,382 B2 | 4/2003 | Wondrak | |
| 6,696,304 B1 | 2/2004 | Davies | |
| 7,794,994 B2 * | 9/2010 | Cranley et al. ................ | 435/190 |
| 2007/0287169 A1 * | 12/2007 | Ahn ................... | G01N 33/6842 |
| | | | 435/68.1 |

(Continued)

OTHER PUBLICATIONS

Lewis et al. (Journal of Biochemical and Biophysical Methods, 1990, 12:129-144).*

(Continued)

*Primary Examiner* — Jeremy C Flinders
(74) *Attorney, Agent, or Firm* — Foley & Lardner LLP; Antoinette F. Konski

(57) ABSTRACT

The present invention relates to a method for detecting and optionally quantifying at least one molecule comprising at least one protonated group such as an amine function immobilized at the surface of the solid substrate, said method being a reversible, direct and colorimetric method that uses a coloring agent. The present invention also relates to various uses of said method and the solutions used during said method.

19 Claims, 2 Drawing Sheets

(56) References Cited

U.S. PATENT DOCUMENTS

2008/0206183 A1  8/2008  Commeyras et al.

OTHER PUBLICATIONS

Orschel et al. (Colloids and Surfaces B: Biointerfaces, 1998, 10:273-279).*
Gosnell et al. (Microchemical Journal, 1988, 37:149-154).*
Shevchenko et al. (Nature Protocols, 2007, 1(6):2856-2860).*
Arkas, et al., "Organosilicon Dentritic Networks in Porous Ceramics for Water Purification", Chemistry of Material, vol. 17, No. 13, pp. 3439-3444 (2005).
Atherton, et al., "A Mathematical Model for the Description of the Coornassie Brilliant Blue Protein Asssay", Analytical Biochemistry, 233, pp. 160-168 (1996).
Bradford, Marion M., "A Rapid and Sensitive Method for the Quantitation of Microgram Quantities of Protein Utilizing the Principle of Protein-Dye Binding", Analytical Biochemistry 72, pp. 248-254 (1976).
Claeys-Bruno, et al., "Methodological approaches for histamine quantification using derivatization by chloroethylnitrosourea and ELISA measurement: Part 1. Optimization of derived histamine detection with coated-plates using optimal design", Chemometrics and Intelligent Laboratory Systems 80:176-185 (2006).
Claeys-Bruno, et al., "Methodological approaches for histamine quantification using derivatization by chloroethylnitrosourea and ELISA measurement. Part II: Optimization of the derivatization step", Chemometrics and Intelligent Laboratory Systems 80:186-197 (2006).
Chial, et al., "A Spectral Study of the Charge Forms of Coomassie Blue G", Analytical Biochemistry 209, pp. 258-266 (1993).
Chial, et al. "A Comparison of the Binding of Coomassie Brilliant Blue to Proteins at Low and Neutral pH", Analytical Biochemistry 213, 362-369 (1993).
Congdon, et al., "The Binding Interaction of Coomassie Blue with Proteins", Analytical Biochemistry 213, pp. 407-413 (1993).
Metwalli, et al., "Surface characterizations of mono-, di-, and tri-aminosilane treated glass substrates", Journal of Colloid and Interface Science 298, pp. 825-831 (2006).
Pathak et al., Dendrimer-Activated Surfaces for High Density and High Activity Protein Chip Applications, Langmuir, vol. 20, No. 15, pp. 6075-6079 (2004).
Hinton et al., "Histological Findings in Amyloidosis of Rabbits," J. Comp. Path., 92:285-294 (1982).
Serrano et al., "Determination of amikacin in body fluid by high-performance liquid-chromatography with chemiluminescence detection," Journal of Chromatography B, 843:20-24 (2006).
Bonde M et al. (1992), "Direct dye binding—a quantitative assay for solid-phase immobilized protein", Analytical Biochemistry, vol. 200, No. 1, Jan. 1992, pp. 195-198.
Coussot G et al. (2009), "Colorimetric quantification of amino groups in linear and dendritic structures", Polymer International, vol. 58, No. 5, Mar. 13, 2009, pp. 511-518.
International Search Report for PCT International Application No. PCT/EP2009/052637 dated Jun. 25, 2009 (3 pages).
Kett W C et al. (2005), "Direct detection of the binding of avidin and lactoferrin fluorescent probes to heparinized surfaces", Analytical Biochemistry, vol. 339, No. 2, Apr. 2005, pp. 206-215.
Lu B et al. (1992), "A Planar Quartz Waveguide Immunosensor Based on TIRF Principle", Analytical Letters, vol. 25, No. 1, Jan. 1992, pp. 1-10.
Marko I E et al. (2003), "Efficient and convergent stereocontrolled spiroannulation of ketones", Tetrahedron Letters, vol. 44, No. 16, Apr. 14, 2003, pp. 3333-3336.
Neuhoff V et al. (1985), "Clear background and highly sensitive protein staining with Coomassie Blue dyes in polyacrylamide gels: A systematic analysis", Electrophoresis, vol. 6, No. 9, pp. 427-448.
Zhu Y et al. (2007), "Density quantification of collagen grafted on biodegradable polyester: Its application to esophageal smooth muscle cell", Analytical Biochemistry, vol. 363, No. 1, Apr. 2007, pp. 119-127.

* cited by examiner

METHOD FOR DETECTING AND QUANTIFYING A MOLECULE INCLUDING AT LEAST ONE PROTONATED GROUP ON A SOLID SUBSTRATE

CROSS REFERENCE TO RELATED APPLICATIONS

The application is a national stage application under 35 U.S.C. §371 of International Application No. PCT/EP2009/052637, filed Mar. 5, 2009, which in turn claims priority to French Application No. 0851425, filed Mar. 5, 2008, the contents of each of which are hereby incorporated by reference into the present disclosure.

TECHNICAL FIELD

The present invention relates to the field of substrates having an interface comprising at least one protonated group, such as an amino and/or protein interface.

More particularly, the present invention is directed toward providing a method and means capable of characterizing the interface comprising at least one protonated group, such as the amino and/or protein interface of these substrates. The method according to the invention is rapid, simple to implement and reversible. This reversibility enables the interface to be used after the implementation of the method of the invention. It has a notable sensitivity and a notable dosage linearity, without affecting the interface, thereby enabling the optional post-characterization use of the substrates thus covered.

PRIOR ART

Various types of substrates exist which have at their surface protonated groups, such as alkyl amines or other amino groups and in particular peptides, polypeptides or proteins in the field of reagents that are of use in biology and, more particularly, in the fields of cell culture, of diagnosis and of biological analyses.

Specifically, substrates which have, at their surface, a matrix consisting of one (or more) protein(s) are substrates that are in particular used in the context of cell culture since they promote adhesion of the cell cultures and, optionally, differentiation thereof. Said substrates are also known as "coated substrates".

Substrates of the peptide chip, protein chip, antibody chip or cell chip type are also tools that are widely used, both in fundamental research and in clinical research. Specifically, such substrates are used for evaluating an immune response and, in particular, for searching for antibodies specific for epitopes or for mimotopes attached to the latter. The detection of molecular interactions also uses substrates of peptide/protein/antibody/cell chip type.

During the preparation or during the use of these substrates which have amino groups at their surface, it is necessary to verify the grafting of the amine functions in the interest of verifying said grafting, the homogeneity thereof or the stability thereof.

U.S. Pat. No. 6,696,304 proposes a method for determining the relative mean amount of a molecule comprising at least one amine, immobilized on a solid substrate. This method uses (1) one (or more) light-emitting label(s) and (2) solid substrates on which known amounts of molecule(s) containing one (or more) amine(s) are immobilized, said solid substrates serving as references. The method which is the subject of U.S. Pat. No. 6,696,304 is, on the one hand, irreversible, as indicated in column 10, lines 29 to 32, and, on the other hand, laborious to implement since it requires the use of standards.

Those skilled in the art are aware of various techniques for quantifying proteins in solution, such as the Lowry method, the Bradford method, the Biuret method, etc.

Coomassie blue is the coloring agent used in the Bradford method for estimating in solution, rapidly, i.e. in a time of less than 5 min, the protein concentration of a medium. The Bradford method makes it possible to assay proteins in solution with detection thresholds of the order of 1 µg of proteins per ml of solution. Under the conditions described by Bradford [Bradford, 1976] using a solution of which the pH is less than 1, the blue-protein complex formed leads to a transfer of the absorption peak, which goes from red ($\lambda_{max}$=470 nm, pH<1) (free cationic form) to green ($\lambda_{max}$=650 nm, pH~1) (neutral form) and then blue ($\lambda_{max}$=595 nm, 2≤pH≤11) (anionic bound form). There is, for Coomassie blue, a "pink-violet" colored $4^{th}$ form ($\lambda_{max}$=530 nm, pH≥11) which up until now has been barely mentioned in the literature. Only one literature reference dating from 1993 makes reference thereto [Chial, 1993]. Furthermore, no assay in solution of one of the 4 free forms of Coomassie blue ($\lambda_{max}$=470, 650, 595 or 530) has in addition been reported in the literature up until now.

U.S. Pat. No. 6,555,382 describes a staining method using Coomassie blue for rapidly visualizing proteins present in a gel, on a membrane or other porous substrate. This staining method uses a solution containing an acid diluted to a concentration of from 1 to 100 mM and Coomassie blue at a concentration of 0.0005% to 0.5% (w/v). However, the invention described in U.S. Pat. No. 6,555,382 enables neither a direct estimation of the amount of protein present per band, nor a quantitative analysis of the number of amines present on the protein "stained", the possibility of detaching the coloring agent having not been mentioned.

No simple, sensitive (<1 µg of protein) and reversible colorimetric method exists for demonstrating and/or quantifying the presence of protonated sites belonging, for example, to proteins, peptides or any molecule comprising at least one amine, which are grafted onto a solid (porous or nonporous) substrate, and which enables the subsequent use of this substrate (i.e. after the demonstration and/or quantification).

DESCRIPTION OF THE INVENTION

The present invention makes it possible to solve the technical problem above by proposing a novel analytical strategy based on direct assaying of a coloring agent. The term "direct assaying" is intended to mean the assaying of the coloring agent "degrafted" from the substrate to be characterized after having bound this colorimetric agent selectively to the amine present at the surface of the substrate and then removed the excess coloring agent. The present invention is directed toward characterizing amino substrates (crude or "coated", i.e. substrates covered with an interface). In the context of the present invention, the term "characterization" is intended to mean not only the detection of amine(s) optionally present at the surface of a solid support, but also the quantification thereof, i.e. the determination of the number of available amines at the surface of this solid substrate. The number of amine functions will be expressed per unit of surface area or per unit of mass of the substrate.

The present invention is noteworthy by virtue of the fact that it applies not only to the field of coated substrates, peptide chips, protein chips, antibody chips or cell chips, but also to any field that uses a solid substrate having at its surface at least one protonated group such as an amine function.

The present invention relates to a method for detecting and optionally quantifying at least one molecule comprising at least one protonated group such as an amine function immobilized at the surface of a solid substrate, said method being a direct colorimetric method that uses a coloring agent.

More particularly, the present invention relates to a method for detecting and optionally quantifying at least one molecule comprising at least one protonated group such as an amine function immobilized at the surface of a solid substrate, comprising the following successive steps:

a) bringing said surface of the solid substrate into contact with a solution $T_1$ containing a coloring agent, b) removing said coloring agent which has not reacted with said surface during step (a), c) bringing said surface into contact with a solution $T_2$ capable of dissociating the possible complex(es) formed between said coloring agent and said molecule comprising at least one protonated group such as an amine function, d) detecting said coloring agent possibly present in the solution $T_2$ so as to detect and optionally quantify said molecule comprising at least one protonated group such as an amine function.

The main steps of the method according to the invention are described schematically in FIG. 1, with Coomassie blue as coloring agent.

In the context of the present invention, the term "coloring agent" is intended to mean a chemical compound which has properties of absorption or emission in the visible light range. By extension, the term "coloring agent" may also denote a compound which has properties of absorption, emission or reemission in a wider range, ranging from near ultraviolet to near infrared, i.e. in a wavelength range of, in general, from 280 to 3000 nm. In addition, the coloring agent that can be used in the context of the present invention consists of any colorant, advantageously organic colorant, capable of reacting with a molecule comprising at least one protonated group such as an amine function.

The coloring agents used in the context of the method according to the invention are in particular chosen from the anthraquinone, mono- and dichlorotriazine, (di)azo derivative and triphenyl-methane families. These families comprise, inter alia, Ponceau Red (or Ponceau S)(CAS No. 6226-79-5), Ponceau 2R (CAS No. 3761-53-3), Ponceau 4R (CAS No. 2611-82-7), Ponceau 6R (CAS No. 2766-77-0), azorubin (CAS No. 3567-69-9), Procion Yellow 4R, Procion rubin (CAS No. 17752-85-1), Brilliant Blue FCF (CAS No. 3844-45-9), Remazol Brilliant Blue (CAS No. 2580-78-1), Fast Green FCF (CAS No. 2353-45-9), Amido Black (CAS No. 1064-48-8), Procion blue (CAS No. 12236-82-7), Serva Violet (CAS No. 910010-03-9), Coomassie blue (CAS No. 78642-64-5 or CAS No. 6104-58-1) and mixtures thereof.

The coloring agent used in the context of the method according to the invention can also be selected from fluorescent agents or phosphorescent agents. These fluorescent agents or these phosphorescent agents are advantageously fluorescent agents or phosphorescent agents which have at least one sulfonate function and/or at least one carboxylate function. By way of examples, and nonexhaustively, mention may be made, among such fluorescent or phosphorescent agents, of fluorescein and derivatives thereof, such as 6-carboxyfluorescein (CAS No. 3301-79-9); eosin Y (CAS No. 17372-87-1); eosin B (CAS No. 548-28-3); rhodamine B (CAS No. 81-88-9), sulforhodamine 101 (CAS No. 60311-02-6), pyranine (CAS No. 6358-69-6) and cardiogreen (Cas No 3599-32-4), etc. . . . .

A coloring agent advantageously used in the context of the present invention is Coomassie blue. Said coloring agent is chosen, more particularly, from the group constituted of Coomassie blue G250, Coomassie blue R250, Coomassie blue R150 and Coomassie blue R350.

Advantageously, the protonated group used in the context of the present invention may be any group bearing a positive fundamental electric charge. More particularly, said positive fundamental electric charge is borne by a nitrogen atom. Thus, the protonated group can be chosen from the group constituted of an amine function, an imine function, a guanidine function and a heteroaryl group.

In the context of the present invention, the term "heteroaryl group" is intended to mean a heteroaromatic carbon-based structure, which is optionally monosubstituted or polysubstituted, constituted of one or more heteroaromatic rings each comprising from 3 to 8 atoms, said structure having a heteroatom N, it being possible for the other optional heteroatom(s) to be N, O, P or S. The substituent(s) may contain one or more heteroatoms, such as N, O, F, Cl, P, Si, Br or S and also alkyl groups, in particular $C_1$ to $C_6$ alkyl groups.

The amine function that can be used in the context of the present invention is a primary amine function of the —$NH_2$ type, a secondary amine function of the —NHR type, (R representing a carbon-based group), or a tertiary amine function of the —NR'R type (R and R' representing identical or different carbon-based groups, or belonging to the same carbon-based group (in the case of cyclic amines)). Preferably, the amine function used in the context of the present invention is a primary amine function of the —$NH_2$ type or a secondary amine function of the —NHR type (R representing a carbon-based group).

The molecule comprising at least one protonated group such as an amine function that can be used in the context of the present invention is any molecule having at least one protonated group such as an amine function that is known to those skilled in the art. This molecule is in particular chosen from the group constituted of peptides, polypeptides, proteins, proteins having prosthetic groups (such as glycoproteins, lipoproteins, nucleoproteins, metalloproteins, chromoproteins or hemoproteins), antibodies, transaminated nucleic acids, biogenic amines, alkylamines, amino polymers, dendrons and dendrimers such as dendrimeric structures of PAMAM (PolyAMidoAMine) type or of PPI (Poly (PropyleneImine)) type or the dendrimeric structures described in International application WO 2006/114528, fragments thereof and derivatives thereof.

By way of examples of proteins that can be used in the context of the present invention and already used as coated-surface interface proteins, mention may be made of streptavidin, gelatin, collagen and in particular collagen type 1, fibronectin, lysozyme, linear polylysine, bovine serum albumin, etc. Moreover, amino polymers of polyacrylamide type, and in particular such as the poly(ethyleneimine)s (PEIs) of formula —$(CH_2—CH_2—NH)_n$— with $10 < n < 10^5$, have also been used as coated-surface interface proteins.

The present invention envisions using derivatives of the molecules containing a protonated group such as an amine function, defined above. The term "derivative" is intended to mean molecules which exhibit 60%, 65%, 70%, 75%, 80%, 85%, 90% and/or 95% identity with the molecules comprising at least one protonated group such as an amine function, defined above and in particular with respect to the nucleotide sequences or to the amino acid sequences of these molecules.

When the molecules comprising at least one protonated group such as an amine function have one (or more) amino acid(s), the derivatives of said molecules can have at least one additional amino acid, a post-translational modification and/or a chemical modification (in particular a glycosylation, an amidation, an acylation, an acetylation, a methylation), or a protective group which makes it possible to prevent their degradation.

The derivatives of the molecules containing a protonated group such as an amine function and having one (or more) amino acid(s) may also be those of which one (or more) amino acid(s) is (are) chosen from the group constituted of enantiomers, diastereoisomers, natural amino acids of D conformation, beta-amino acids, alpha-amino acids which are substituted, rare amino acids, in particular hydroxyproline, hydroxylysine, allohydroxylysine, 6-N-methyllysine, N-ethylglycine, N-methylglycine, N-ethylasparagine, alloisoleucine, N-methylisoleucine, N-methylvaline, pyroglutamine and aminobutyric acid, and synthetic amino acids, in particular ornithine, norleucine, norvaline, cyclohexylalanine and omega-amino acids.

The fragments of the molecules comprising at least one protonated group such as an amine function are, by way of examples and nonexhaustively:
  peptide fragments advantageously having more than 8 amino acids, in particular more than 10 amino acids or else more than 15 amino acids,
  antibody fragments comprising at least the variable domain of a heavy chain (VH) and/or the variable domain of a light chain (VL) of a conventional immunoglobulin, or else the variable domain of a single-chain immunoglobulin, such as the Fab, Fv, scFv or VHH fragments,
  fragments of transaminated nucleic acids advantageously having more than 5 nucleotides, in particular more than 10 nucleotides or else more than 15 nucleotides.

The molecules containing a protonated group such as an amine function, the derivatives thereof and the fragments thereof as defined above can be natural products, or recombinant products obtained according to molecular biology and genetic engineering techniques well known to those skilled in the art, or can be synthesized chemically according to techniques such as solid-phase or liquid-phase synthesis also well known to those skilled in the art.

In the context of the present invention, any solid substrate at the surface of which one (or more) molecule(s) comprising at least one protonated group such as an amine function can be immobilized is capable of being used in the context of the present invention.

In one variant of the invention, the solid substrate or at least the surface of said solid substrate where the molecule (s) comprising at least one protonated group such as an amine function is (are) immobilized, is in particular an inorganic solid substrate or surface. Specifically, it is possible to envision a solid substrate of which only the surface is made of a particular inorganic material, the rest of the substrate being made of another inorganic material or made of an organic material. Advantageously, the solid support or the surface of said solid support is made of an inorganic material chosen from the group constituted of glasses, quartzes, ceramics (for example, of oxide type), metals (for example, aluminum, chromium, copper, zinc, silver, nickel, tin or gold), metalloids (for example, silicon or silicon oxide) and mixtures thereof.

In another variant of the invention, the solid substrate or at least the surface of said solid substrate where the molecule(s) comprising at least one protonated group such as an amine function is (are) immobilized is made of an organic material, for instance a polymer, such as agarose, or a resin, including nylon, polyethylene glycol, polycarbonates, polyfluoropolymers or composites. It is also possible to envision a solid substrate of which only the surface is made of a particular organic material, the rest of the substrate being made of another organic material or of an inorganic material.

Said solid substrate may be in various forms of varying size. By way of examples, and nonexhaustively, it may be in the form of slides, microplates, particles, gels, such as an agarose gel, beads, microbeads, fibers, tubes, such as hemolysis tubes, or microchannels of capillary type. These various types of substrate can have sizes ranging from a few hundred micrometers to several centimeters.

In one particular embodiment of the present invention, the solid substrate has a surface bearing functional groups by virtue of which the molecule(s) comprising at least one protonated group such as an amine function is (are) capable of being immobilized. Advantageously, these functional groups are chosen from carboxylic groups, radical entities, alcohol functions, amine functions, amide functions, epoxy functions or thiol functions. This functionalization may be intrinsic to the nature of the material at the surface of the solid substrate used. Alternatively, this functionalization may be obtained by cleaning said surface by means of at least one solvent, detergent, radiation or plasma or any other method for forming functional groups as defined above.

In a first variant of the present invention, the molecule comprising at least one protonated group such as an amine function can be immobilized directly at the surface of the optionally functionalized solid substrate. A solid substrate "coated" with a protein is an example of direct immobilization.

In a second variant of the present invention, the molecule comprising at least one protonated group such as an amine function can be immobilized indirectly at the surface of the optionally functionalized solid substrate. This indirect immobilization involves a spacer arm (or joining agent) bound, on the one hand, to the solid substrate and, on the other hand, to the molecule comprising at least one protonated group such as an amine function. The spacer arm may or may not react with the coloring agent during step (a) of the method according to the invention and in particular may or may not have a protonated group such as an amine function capable of reacting during said step (a). Those skilled in the art are aware of various examples of such spacer arms. Nonexhaustively, mention may be made, as spacer arms capable of being used in the context of the present invention, of 1,6-diaminohexane, 6-aminohexanoic acid, a succinimide group, an epoxide, UDP-glucuronic acid, linear or branched alkyl chains containing from 1 to 20 carbon atoms, polyethylene glycol, glutaraldehyde, etc.

The bonds used during a direct or indirect immobilization may be any bonds known to those skilled in the art, and in particular covalent bonds, ionic bonds, hydrogen bonds, an adsorption, etc.

The first step of the method according to the invention (step a), termed "staining" step, consists in bringing the surface capable of exhibiting a molecule comprising at least one protonated group such as an amine function into contact with a given concentration of coloring agent. Said coloring agent is diluted in the solution $T_1$.

The solution $T_1$ is a solution commonly used during staining which uses one of the coloring agents as defined above, in particular during assaying in solution, staining of SDS-PAGE electrophoresis gels or staining of cellulose membranes. Those skilled in the art will therefore know, depending on the coloring agent used, which solution $T_1$ to use (nature and amount of the components).

Advantageously, the solution $T_1$ is an aqueous solution comprising an alcohol and/or an acid. The pH of the solution $T_1$ is advantageously greater than 1 and, in particular, greater than 2.

The alcohol contained in the solution $T_1$ is advantageously chosen from the group constituted of methanol, ethanol, propanol, isopropanol, butanol and mixtures thereof. The proportion of alcohol is between 1% and 25%, especially between 2% and 20%, and in particular between 5% and 15% by volume, relative to the total volume of solution $T_1$.

The acid contained in the solution $T_1$ is advantageously chosen from the group constituted of acetic acid, trichloroacetic acid, phosphoric acid, hydrochloric acid, sulfuric acid, perchloric acid and mixtures thereof. The proportion of acid is between 0.5% and 20%, especially between 1% and 15%, and in particular between 2% and 10% by volume, relative to the total volume of solution $T_1$.

The coloring agent as defined above is used in an amount of between 0.001% and 1%, especially between 0.005% and 0.5%, and in particular between 0.01% and 0.1% by mass, relative to the total volume of solution $T_1$.

Step (a) of the method according to the invention is advantageously carried out at ambient temperature (i.e. a temperature between 20 and 25° C.), with agitation. The duration of step (a) according to the invention is greater than 3 min, especially greater than 5 min, in particular between 5 min and 2 hours, more particularly between 5 min and 1 hour, and most particularly between 5 and 30 min.

By way of example and when the coloring agent used is Coomassie blue, the solution $T_1$ is composed of 85% of milliQ water, 10% of analytical quality methanol and 5% of analytical quality acetic acid, and its pH is 2.2. The Coomassie blue (G-250) is used at 0.05% by mass in this solution during the staining step.

In order for there to be a maximum of interactions of the Coomassie blue with the molecule comprising at least one protonated group such as an amine, immobilized on a solid substrate, and in particular with said amines, the coloring agent has been used in the solution $T_1$ at a concentration C which is much higher than that used during the assaying in solution by means of the Bradford test. This concentration C greater than or equal to 500 µg/mL does not enable assaying in solution since there is then saturation of the absorbance signal during the direct reading. Employing a concentration of 500 µg/mL of Coomassie blue makes it possible to reuse the solution $T_1$. In addition, the solution $T_1$ which contains a high concentration of Coomassie blue avoids steps of setting up according to the format used; it can therefore be used on formats which have higher binding capacities than the microplate formats tested in the present invention.

On the basis of this teaching and of the knowledge of those skilled in the art, the latter will be able to choose an amount of coloring agent, other than Coomassie blue, suitable for obtaining the advantages mentioned above.

Step (b) of the method according to the invention is directed toward removing the coloring agent which has not reacted, and in particular which has not formed complexes with the molecule comprising at least one protonated group such as an amine function. This step (b) consists of a step comprising at least one wash.

Advantageously, step (b) of the method according to the invention comprises one (or more) wash(es) of the surface of the solid substrate on which one (or more) molecule(s) comprising at least one protonated group such as an amine function is (are) immobilized, by means of identical or different washing solutions. In particular, step (b) of the method according to the invention comprises at least two washes, at least three washes, at least four washes or at least five washes of said surface of the solid substrate. Those skilled in the art will readily know how to define the necessary and sufficient number of washes according to the coloring agent and its concentration used during step (a) of the method and according to the washing solution(s) used. Thus, those skilled in the art will be able to recover the washing solutions and verify, in particular by means of a spectrophotometric measurement, the presence of coloring agent in said solutions. As soon as the washing solutions no longer contain any coloring agent, step (b) of the method according to the invention is complete.

The washes may be carried out with an identical or different washing solution. Specifically, it is possible to envision using, during step (b), a washing solution which is identical at each wash, washing solutions which are different from one wash to another or washing solutions which are identical or different from one wash to another. The washes may be for identical or different periods of time, these periods extending from a few minutes (2, 3, 5, 10 or 15 minutes) to one (or more) hour(s) (1, 2, 3, 4, 5 or 15 hours). Step (b) of the method according to the invention is advantageously carried out with agitation and at ambient temperature, but can also be carried out at a temperature below ambient temperature, and in particular in a cold room (temperature of between 3 and 6° C.)

Any washing solution known to those skilled in the art can be used in the context of step (b) of the method according to the invention. The only condition is that this washing solution affects neither the immobilization of the molecule(s) comprising at least one protonated group such as an amine function at the surface of the solid substrate, nor the possible complexes formed between the coloring agent used in step (a) and said molecule comprising at least one protonated group such as an amine function.

By way of examples and nonexhaustively, the washing solution used during step (b) of the method is chosen from the group constituted of water, distilled water, demineralized water, deionized water, a phosphate buffered saline (or PBS), a saline solution (such as NaCl), an acetate buffer (such as AcONa), a carbonate buffer (such as $NH_4HCO_3$ or $NaHCO_3/Na_2CO_3$), or an aqueous solution comprising an alcohol and/or an acid (i.e. the solution $T_1$ without coloring agent) as defined above, and mixtures thereof.

Advantageously, the first wash during step (b) of the method according to the invention is preceded by the removal of the solution $T_1$ containing the coloring agent then in contact with the surface of the solid substrate. This removal may in particular be carried out by tapping, by absorption or by drawing-up.

In one particular embodiment, the final wash is carried out with water, and in particular distilled, demineralized and/or deionized water (such as water purified on the Milli-Q® system from the company Millipore, hereinafter denoted "Milli-Q water").

After the final wash of step (b) of the method according to the invention, the surface of the solid substrate can be dried before being brought into contact with the solution $T_2$ during step (c).

The spectrophotometric analysis of the coloring agent/protonated group such as amine complex, after step (b) of the method of the invention, was not conclusive. This is because the complexes between the molecule comprising at least one protonated group such as an amine function and the coloring agent, in particular Coomassie blue, could not be detected on a spectrophotometer because they were below the detection threshold of the method. It should be recalled that, in solution and under the Bradford conditions, the detection limit is in the region of 1 µg/mL, i.e., for microplate wells, 0.15 µg/well. However, after immobilization on a solid substrate of an interface of molecules comprising at least one protonated group such as an amine function having a molecular weight of 21 500 Da, the inventors calculated that, according to a simplified model, the monolayer on the bottom of the well would not exceed 0.02 µg. Direct readings of the molecule-Coomassie blue complex on the solid substrate cannot therefore be envisioned.

Step (c) of the method according to the invention, termed "destaining" step, consists in returning to solution the coloring agent having interacted with the molecule(s) comprising at least one protonated group such as an amine function, present at the surface of the substrate, by means of a solution $T_2$. This step makes the method of the invention "reversible" by enabling reuse of the substrate after its characterization.

The solution $T_2$ is therefore a solution capable of dissociating the possible complexes between the coloring agent and the molecule(s) comprising at least one protonated group such as an amine function, present at the surface of the substrate. The composition of the solution $T_2$ was optimized so as to detach all of the coloring agent considered to be bound to the surface during staining step (a).

Attempts to dissociate the complexes between the coloring agent and the molecule comprising at least one amine function, the substrate used being a polystyrene plate, were carried out using strong washes with either water, acetate (AcONa), ammonium bicarbonate (NH4HCO3) and sodium bicarbonate/carbonate (NaHCO3/Na2CO3) buffers at various molarities and at pHs ranging up to 11.5, saline solutions (NaCl (3M)), mixed NaCl/carbonate buffer solutions, or alcoholic solutions ranging up to 50% alcohol (such as methanol or acetonitrile (ACN)). These attempts applied to polystyrene substrates remained unsuccessful and did not make it possible to detach the coloring agent from the solid substrate.

The mixtures in the presence of ACN were eliminated owing to the low chemical resistance to ACN of many polymer materials (in particular, polystyrene, the basic material of many microplates) that may be used for the solid substrate or its surface.

The inventors demonstrated that a water/organic solvent mixed solution called T2 makes it possible to dissociate the complexes between the coloring agent and the molecule comprising at least one protonated group such as an amine function. Advantageously, the solution $T_2$ capable of detaching the coloring agent instantaneously and quantitatively is an aqueous solution containing an organic solvent and a constituent chosen from sodium hydroxide, caustic potash (or potassium hydroxide), and carbonate ions, and mixtures thereof. Particularly advantageously, said solution $T_2$ is an aqueous solution containing an organic solvent and carbonate ions.

The pH of the solution $T_2$ is advantageously greater than 9, especially greater than 10, in particular greater than 11, and more particularly greater than 11.25.

Any organic solvent known to those skilled in the art can be used in the solution $T_2$ employed in the present invention. Those skilled in the art will know, without an inventive step being involved, how to choose the organic solvent that is most suitable according to the substrate, the coloring agent and the molecules bearing an amine function used. Preferably, the organic solvent used in the solution $T_2$ is an alcohol. The alcohol contained in the solution $T_2$ is advantageously chosen from the group constituted of methanol, ethanol, propanol, isopropanol and butanol and mixture thereof. The proportion of alcohol is between 10% and 80%, especially between 25% and 70%, and in particular between 40% and 60% by volume, relative to the total volume of solution $T_2$.

The solution $T_2$ comprises, in addition to the organic solvent, sodium hydroxide (NaOH), caustic potash (KOH), carbonate ions, or mixtures thereof. The carbonate ions, hydroxide ions, potassium ions or sodium ions contained in the solution $T_2$ have a molarity of between 0.001 and 1 M, especially between 0.005 and 0.5 M, in particular between 0.01 and 0.1 M. The carbonate ions of the solution $T_2$ used in the method according to the invention are advantageously in the form of ammonium bicarbonate ($NH_4HCO_3$), of sodium bicarbonate and carbonate ($NaHCO_3/Na_2CO_3$) or of potassium carbonate ($K_2CO_3$), etc. . . . , or of mixtures thereof.

Step (c) of the method according to the invention is carried out at a temperature of between 4 and 50° C., and more advantageously at 20° C., with agitation. The duration of step (c) according to the invention is greater than 1 second and less than 5 min.

The volume of solution $T_2$ will have to be selected in such a way as to completely cover the surface to be characterized. This volume to be introduced during step (c) must, however, not be too great, so as to prevent too great a dilution of the coloring agent and allow it to be assayed during step d). A step of concentrating, advantageously by evaporation, can be envisioned, subsequent to step (c) and prior to step (d), if large destaining volumes have been necessary.

Step (d) of the method of the invention consists in detecting the coloring agent present in the solution $T_2$ recovered after step (c), i.e. the solution $T_2$ as defined above, also comprising the coloring agent derived from the dissociation of the complex between the molecule comprising at least one protonated group such as an amine function and the coloring agent, during step (c) of the method.

Before step (d), the solution $T_2$ also comprising the coloring agent recovered during step (c) can advantageously be subjected to an acidification or a basification. This additional step makes it possible in particular to modify the pH of the solution $T_2$ also comprising the coloring agent recovered during step (c), in order for the pH conditions to be optimal with a view to the detection and optionally the quantification of said coloring agent.

The detection of the coloring agent during step (d) of the method according to the invention consists in measuring the optical density (or absorbance) of the solution $T_2$ obtained after step (c). The optical density of this solution is determined using a spectrophotometer calibrated beforehand to the absorption wavelength of the coloring agent used. Such a detection is routine work for those skilled in the art, who will know, depending on the coloring agent used and on the pH of the solution $T_2$, the absorption wavelength at which the detection in step (d) should be carried out.

Furthermore, it is clear that, the optical density obtained, under the same conditions, in the absence of the molecule comprising at least one protonated group such as an amine function should be subtracted from the optical density obtained during step (d) of the method according to the invention. In the context of the present invention, the expression "under the same conditions" is intended to mean same support, same steps (a) to (d), i.e. same solutions $T_1$ and $T_2$, and identical coloring agent and amount used, same washing buffer(s), same temperatures, duration and condition for each of the steps. The value obtained after said subtraction is called "real optical density" or "real absorbance". The optical density measured in the absence of molecule(s) comprising at least one protonated group such as an amine function makes it possible to assess the background noise of the measurement and the complexes possibly formed between the coloring agent and the solid substrate, its optional functional groups, the optional spacer arms and/or molecules comprising at least one protonated group such as an amine function optionally immobilized on the solid substrate and different than the molecules comprising at least one protonated group such as an amine function for which the method of detection and optionally of quantification according to the invention is used.

An optical density obtained during step (d) of the method according to the invention in the presence of possible molecule(s) comprising at least one protonated group such as an amine function which is greater than the optical density obtained, under the same conditions, in the absence of molecule(s) comprising at least one protonated group such as an amine function, makes it possible to conclude that at least one molecule comprising at least one protonated group such as an amine function is immobilized at the surface of the solid substrate.

The quantification of the molecule(s) comprising at least one protonated group such as an amine function on the basis of the real optical density obtained during step (d) of the method according to the invention can be obtained on the basis of calibration curves or by calculation, as presented hereinafter and in particular with Coomassie blue used as coloring agent.

Thus, step (d) of the method according to the present invention may comprise the following substeps consisting in:

i) measuring the "real absorbance" (or "real optical density") of the coloring agent in the solution $T_2$ optionally acidified or basified beforehand;

ii) deducing, from the "real absorbance" measured in substep (i), the amount and/or the concentration of coloring agent present in the solution $T_2$, in particular on the basis of standard curves of the absorbance of said coloring agent as a function of its amount and/or of its concentration;

iii) deducing, from the amount and/or from the concentration of coloring agent obtained in substep (ii), the amount and/or the concentration of protonated groups such as amine functions and/or of molecules comprising at least one protonated group such as an amine function.

Substep (iii) of the method according to the invention can be carried out having previously determined the number of molecules of coloring agent capable of binding to a protonated group as defined above and/or to a molecule comprising at least one such protonated group. This prior determination is in particular based on the Beer-Lambert law which defines the change in absorbance ($\Delta A$) observed when molecules comprising a protonated group are added to a solution of coloring agent, by equation (1) below:

$$\Delta A = (a_{Bound} - a_{Free}) l D_{Bound} \tag{1}$$

in which:

$a_{Bound}$ and $a_{Free}$ are the molar extinction coefficients, respectively, of the bound coloring agent and of the free coloring agent;

l is the length of the optical path in the solution passed through (by way of example, when the experiments are carried out in a well of a 96-well microplate, l corresponds to the height of the solution in the well and is of the order of 1.05 cm for 300 µL of solution) and $D_{Bound}$ is the concentration of bound coloring agent.

More particularly, this prior determination may comprise one or more of the following steps consisting in:

α) determining the molar extinction coefficient $a_{Free}$ on the basis of the real absorbance obtained for solutions containing various amounts or concentrations of coloring agent and of the Beer-Lambert law;

β) determining the molar extinction coefficient $a_{Bound}$ in the presence of an excess of molecules comprising at least one protonated group; in this case, all the coloring agents are considered to be bound ($D_{Bound}$) to the sites of the molecules such that $D_{Bound}$ equals the initial concentration of coloring agent ($D_T$). Thus, the Beer-Lambert equation (1) becomes the following equation (2):

$$\Delta A = (a_{Bound} - a_{Free}) l D_{Bound} = (\Delta a) l D_T \tag{2}$$

in which $\Delta a$ is the difference in the molar extinction coefficients $a_{Bound} - a_{Free}$.

The Atherton mathematical model is used during the determination of $a_{Bound}$. The values of $\Delta a$ and of $a_{Bound}$ can be obtained from the double-reciprocal representation of the reciprocal change in absorbance ($1/\Delta A$) as a function of the reciprocal amount or concentration ($1/\Delta P_T$) of molecules comprising at least one protonated group at a selected constant concentration of coloring agent ($D_T$);

ε) determining the total number of binding sites ($n_{Total}$) in the presence of an excess of coloring agent;

this is because an excess of coloring agent favors saturation of the binding and a maximum number of binding sites are occupied by said coloring agent, i.e. $n = n_{Total}$. Thus, $D_T \gg n_{Total} P_T$ with $P_T$ representing the molar concentration of molecules comprising at least one protonated group, which leads to $D_{Bound} = n_{Total} P_T$ and the Beer-Lambert equation (1) becoming the equation (3) below:

$$\Delta A = (\Delta a) l \, n_{Total} P_T \tag{3}$$

$n_{Total}$ can therefore be determined, in the presence of an excess of coloring agent, from the curve $\Delta A$ as a function of $P_T$, as long as this curve is linear. Thus, if and only if the theoretical total number of binding sites has been previously determined by means of another independent analytical method, the percentage of sites occupied by the coloring agent can be calculated per molecule comprising at least one protonated group.

By way of example and when the coloring agent used is Coomassie blue, the solution $T_2$ is a solution composed of 50% of analytical quality methanol and 50% of a 0.1 M solution of carbonate ions, advantageously in the form of sodium bicarbonate/carbonate at a pH of greater than or equal to 11.25. Under these conditions, the Coomassie blue returns to solution in its "pink-violet" colored 4th form ($\lambda_{max}$ around 530 nm, pH≥11) barely mentioned up until now in the literature. In the solution $T_2$, the free Coomassie blue has a maximum absorption at 520 nm. The measurements are carried out after the addition of 20 µL of HCl (3 N) to the buffer $T_2$, the pH is then 6.1. The free form of Coomassie blue turns blue and has a stable maximum absorption at 610 nm. It should be noted that, given the absorption spectrum of Coomassie blue in the acidified buffer $T_2$, the maximum absorption ranges between 610 and 630 nm and that, therefore, the absorbance measurements can be carried out at any wavelength included in this range, without the result being substantially affected, it being considered that the calibration range is realized at the same wavelength. The number of molecules of Coomassie blue detected can then be correlated to the density of protonated groups such as amines that are available on the surface to be characterized, since the complexes formed between the Coomassie blue and the molecule comprising at least one protonated group such as an amine function are more particularly formed between the Coomassie blue and said protonated group such as an amine function.

With the aim of quantifying the number of protonated sites such as amines that are present at the surface of the substrate, the inventors prepared standard solutions of Coomassie blue in the acidified solution $T_2$ (pH 6.1, $\lambda_{max}$=610 nm). The response is linear for a concentration of Coomassie blue of up to 15 µg/mL, and in particular of between 0.5 and 15 µg/mL. The limit of quantification for microplate wells is then 39.5 ng/mL (coefficient of variation (CV)<2%; n=64). This represents a minimum of $10^{13}$ Coomassie blue molecules quantifiable per $cm^2$. The values reported in FIG. 2A are the mean of 6 measurements carried out in the same day. The standard deviations on the measurement are less than 0.02 absorbance units. These ranges were repeated several times on different days and with n=3 different handlers (intermediate fidelity, slope=0.0802, CV<1%). The tests with reduced residues showing a very random distribution of the values are reported in FIG. 2B.

In the context of this approach, the inventors sought to define the maximum number of Coomassie blue molecules capable of interacting per molecule having at least one protonated group such as an amine function during the formation of complexes between this molecule and the Coomassie blue. The purpose is to define a ratio of number of Coomassie blue molecules per number of protonated groups such as amines.

According to the research team of Splittgerber [Chial, 1993] [Congdon, 1993], in a homogeneous medium, the mean number of Coomassie blue molecules bound per protein molecule is given by the equation (Eq. 3).

In the case of the present invention, in the solution $T_1$, the number of Coomassie blue molecules is in very large excess. The value of $n_{total}$ representing the total number of Coomassie blue molecules having interacted with the surface protonated groups such as amines of the solid substrate is determined during the destaining step of the present invention, i.e. during the assaying of the Coomassie blue after detachment in the solution $T_2$. This value is therefore directly proportional to the number of protonated groups such as amines of the substrate having reacted during step (a) of the method.

According to a mathematical model with two levels of Coomassie blue concentration described by Atherton [Atherton, 1996], the inventors demonstrated that, under saturation conditions, the percentage of sites occupied by the Coomassie blue was 93% on bovine serum albumin, 93.5% on linear poly(lysine), 91.7% on a $2^{nd}$-generation lysine dendrimer, 92.7% for the $3^{rd}$-generation dendrimer and 89.9% for the $4^{th}$-generation dendrimer, and 96.9% for a $5^{th}$-generation PAMAM-type dendrimer, i.e. there is at most one molecule of blue per protonated group such as $NH_2$.

On the basis of the above teaching, those skilled in the art can implement the present invention, without an inventive step being involved, using a coloring agent other than Coomassie blue, and in particular a coloring agent capable of forming complexes with a molecule comprising at least one protonated group, such as an amine function, without said group being directly involved in the complex formed.

There are multiple and varied applications of the present colorimetric invention.

Thus, the present invention relates to the use of the method as defined above, for comparing various strategies (or protocols) for immobilizing molecules comprising at least one protonated group such as an amine function on solid substrates and capable of generating coated substrates, peptide chips, protein chips, antibody chips or cell chips.

The present invention also relates to the use of the method as defined above, for verifying whether the coated substrates, the peptide chips, the protein chips, the antibody chips or the cell chips meet all the criteria of analytical quality. This is because the present invention makes it possible to verify all the analytical quality criteria represented by:

the stability of the substrate covered with an interface comprising one or more molecule(s) comprising at least one amine function, with respect to the washing and/or staining/destaining cycles of the present invention, the robustness (repeatability and reproducibility) of the grafting of said interface in the fabrication of coated substrates, of peptide chips, of protein chips, of antibody chips or of cell chips (intra- and inter-experiment homogeneity), the sensitivity by comparison with the commercially available coated substrates, peptide chips, protein chips, antibody chips or cell chips, etc.

The present invention also relates to the use of the method as defined above, for detecting and optionally quantifying molecules comprising at least one protonated group such as an amine function, and more particularly proteins, antibodies or fragments thereof present in a liquid of interest. In the context of the present invention, the term "liquid of interest" is intended to mean a cell culture medium, or a biological fluid isolated or extracted beforehand from the human or animal body (of the blood, lymph, urine, saliva, sperm, etc., type). The implementation of this particular application comprises the following successive steps:

preparing a solid substrate having, at its surface, at least one antigen or at least one antibody specific for the protein, for the antibody or for their fragments being sought;

bringing the substrate thus prepared into contact with the liquid of interest;

step (a) of the method according to the invention as defined above;

step (b) of the method according to the invention as defined above;

step (c) of the method according to the invention as defined above;

step (d) of the method according to the invention as defined above.

It is clear that, during the implementation of step (d), and with a view to detecting or quantifying at least one protein, at least one antibody or at least one of their fragments present in a liquid of interest, the real optical density as defined above is obtained by subtracting, from the optical density obtained in step (d), the optical density obtained after implementation of the method according to the invention on the solid substrate having, at its surface, at least one antigen or at least one antibody specific for the protein, for the antibody or for their fragments being sought.

The present invention also relates to the solution $T_1$ as defined above, containing a coloring agent as defined above in an amount of greater than or equal to 0.05% by mass, relative to the volume of the solution $T_1$.

The present invention also relates to the solution $T_2$ as defined above, i.e. a solution comprising an alcohol and carbonate ions.

The present invention relates to a kit of constituents such as an assay kit for carrying out the method according to the invention, containing:
  in a first compartment, the solution $T_1$ as defined above;
  in a second compartment, the solution $T_2$ as defined above;
  and, optionally, one (or more) washing solution(s) as defined above.

Advantageously, the kit of constituents according to the invention comprises:
  in a first compartment, the solution $T_1$ as defined above;
  in a second compartment, the solution $T_2$ as defined above;
  in a third compartment, a washing solution as defined above;
  in a fourth compartment, a solution for acidifying the solution $T_2$.

In the context of the present invention, the term "compartment" is intended to mean a single container such as a bottle, or a set of containers, which may be identical or different, containing the same solution, such as vials.

A particular example of a kit of constituents according to the invention and in particular that can be used for carrying out 320 measurements, comprises:
  in a first compartment, 100 ml of Coomassie blue at 500 mg·mL$^{-1}$ in an acetic acid/methanol/ultrapure water buffer (v:v:v; 5:10:85) (reagent A);
  in a second compartment, 100 ml of 0.25 M carbonate buffer, pH 11.25, at 50% in methanol (reagent B);
  in a third compartment, 750 ml of a washing solution comprising acetic acid/methanol/ultrapure water (v:v:v; 5:10:85) (reagent C);
  in a fourth compartment, 8 vials of 1 ml of hydrochloric acid (3N),
it being possible for said kit to be accompanied by a precise instruction leaflet for the protocol to be followed for the principle of the measurement and also advice in the event of problems during the use of the kit or of the method, of the troubleshooting type.

Finally, the present invention relates to the use of the solution $T_1$ as defined above, of the solution $T_2$ as defined above, of the "pale pink-violet" form of Coomassie blue which has a maximum absorption at 520 nm and/or of the "turquoise blue" form of Coomassie blue which has a maximum absorption at 610 nm, for detecting and optionally quantifying, directly, at least one molecule comprising at least one protonated group such as an amine function immobilized at the surface of a solid substrate.

Other characteristics and advantages of the present invention will further emerge on reading the examples hereinafter, given by way of nonlimiting illustration.

DETAILED DESCRIPTION OF PARTICULAR EMBODIMENTS

Example 1

Characterization of a Commercial Substrate Exhibiting Alkylamines ($NH_2$)

1. Material
  Format: 96-well microplates;
  Material: polystyrene;
  Coating: alkylamine (terminal primary amine), Amine™ Corning (#2388).

2. Characterization Protocol
  Preliminary step—conditioning: 300 µL of solution $T_1$ (85% of milliQ water, 10% of analytical quality methanol, 5% of analytical quality acetic acid) are introduced per well. This solution is left in contact in the wells, with agitation, for 15 min, at ambient temperature.

Step (a) of the method of the invention: 100 µL of Coomassie blue (G250) at 500 µg/mL in the solution $T_1$ are introduced per well. This solution is left in contact in the well, with agitation, for 15 min, at ambient temperature, in the dark.

Step (b) of the method of the invention: the wells are emptied, rinsed three times with 300 µL of $T_1$, and then 300 µL of $T_1$ are added per well. This solution is left in contact in the well, with agitation, for 15 min, at ambient temperature.

Step (c) of the method of the invention: the wells are emptied. A Maxisorp™ native microplate (Nunc) is prepared with 20 µL of 3N hydrochloric acid per well. The plate having previously interacted with Coomassie blue is "destained" with 300 µL of buffer $T_2$ (50% of 0.1 M carbonate buffer, pH 11.25, containing 500 of analytical quality methanol), and 270 µL are removed at a time of less than 5 min so as to be deposited on the Maxisorp™ plate previously prepared.

Step (d) of the method according to the invention: the absorbance of the acidified recovered solutions is then measured at 620 nm. In the examples which follow, the real absorbances are considered. The real absorbances are the result of the difference between the absorbances read and those of the background noises obtained under the same conditions (for example, same buffer solution, but without Coomassie blue, etc. . . . ).

3. Results

TABLE 1

| | $NH_2/cm^2$ given by the manufacturer | $NH_2/cm^2$ measured by the invention |
|---|---|---|
| Amine ™ Corning | $2 \times 10^{13}$ | $0.27 \times 10^{13} \pm 2\%$ (n = 48) |

The results given in Table 1 above show that the invention makes it possible to determine the number of surface amines in a sensitive and repeatable manner.

The total characterization time was 55 minutes for 48 wells; it is a minimum of 50 min for one well. No laborious material is required to carry out this assay, which can be easily carried out in 4 steps. The present invention is therefore simple to implement, rapid and repeatable.

Example 2

Figure 1:
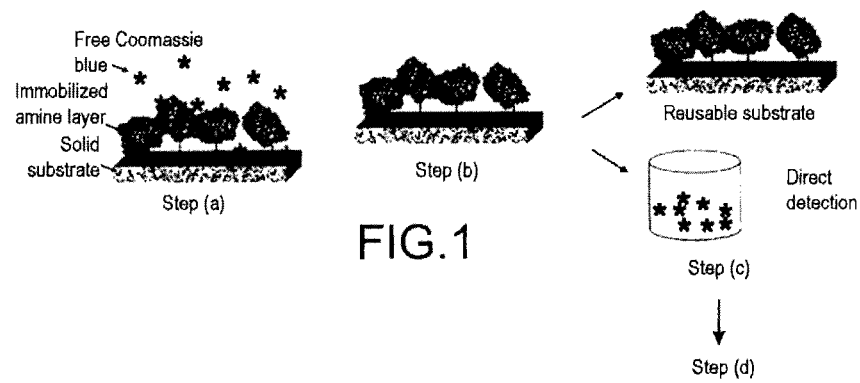
FIG. 1 is a schematic representation of the main steps of the method according to the invention.
Figure 2A:
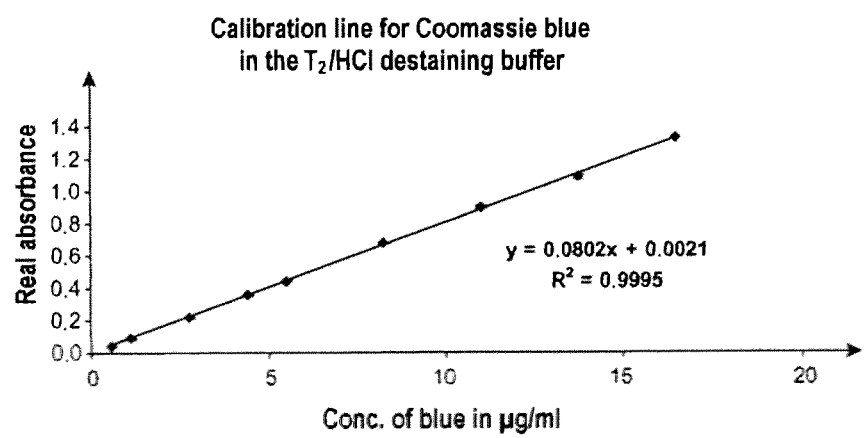
FIG. 2 shows the determination of the linearity range for Coomassie blue in the solution $T_2$/HCl (FIG. 2A) and the test with reduced residues (FIG. 2B).
Figure 2B:
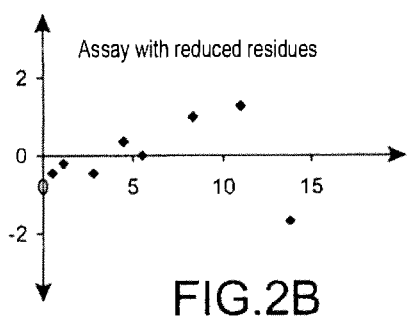

Linearity, Limit of Quantification (LOQ) and Robustness of the Method Described by the Present Invention 1. Study of Linearity The linearity of the method according to the invention has already been discussed (see FIG. 2).

2. Coefficient of Variation at the LOQ

The LOQ was estimated by measuring a volume of 290 µL of a solution $T_2HCl$ (as defined in Example 1) corresponding to a blank with LOQ=$OD_{blank}$+10*$\sigma_{ODblank}$, on 16 measurements.

Once this LOQ had been estimated, 4 solutions of Coomassie blue were prepared at the LOQ in the solution $T_2HCl$ by three different handlers using commercial Coomassie blue (G-250). These 4 solutions were measured 16 times (290 µL/well) at 620 nm.

Results

The LOQ is 39.5 ng of Coomassie blue/mL, it being possible for this LOQ to be improved by concentrating the solution by evaporation before carrying out the measurement.

The coefficient of variation at the LOQ is 1.64% (n=64, reproducibility).

3. Fidelity of the Stock Solution Coomassie Blue in $T_1$ 7 stock solutions of Coomassie blue in $T_1$ (500 µg/mL) were prepared by 4 different handlers, over 10 days. The ODs of these 7 solutions were measured after dilution to 1/50 in $T_1$ (270 µL, at 620 nm). These solutions were then used to "stain" Amine™ plates from Corning as described in Example 1.

Results

The OD of the stock solutions of Coomassie blue in $T_1$ is between 0.39-0.5 absorbance unit.

The staining of the plates with the two extreme solutions prepared (OD 0.39 and OD 0.5) resulted in an OD, respectively, of 0.168±<2% and 0.167±<2% (n=8 in the two cases). These results show that the preparation of the stock solutions of Coomassie blue results in reproducible stainings.

4. Robustness of the Measurement as a Function of the pH of the Buffer $T_2$+HCl The influence of the molarity of the HCl (1-6N) and of the volume of HCl (5.4%-12%) in $T_2$ corresponding to pHs of between 0.1-11.2 was tested.

Figure 3:
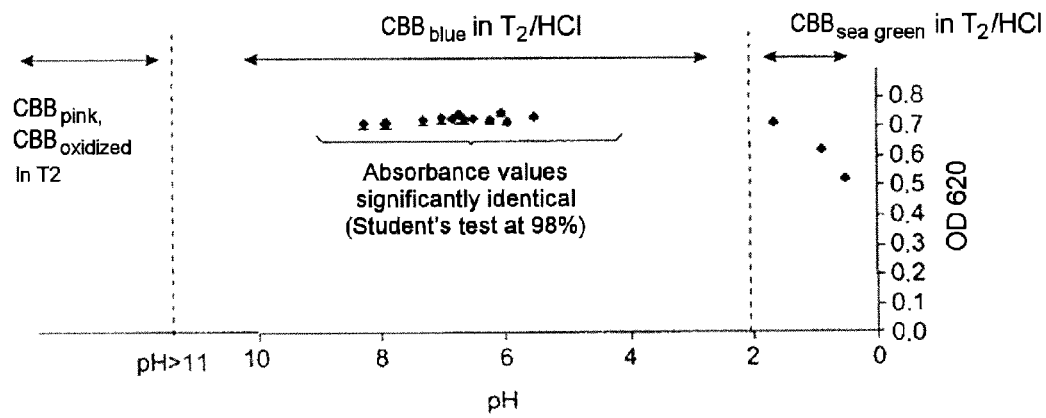
FIG. 3 shows the absorbance value for Coomassie blue in the solution $T_2$/HCl, measured at 620 nm, as a function of the pH of said solution $T_2$/HCl.

The results show (FIG. 3) that a variation of 5.7% (corresponding to ±1.1 µL of 3N HCl) in the volume of 3N HCl added to $T_2$ does not induce any significant difference (Student's test at 98%) in the OD measured.

All these results show that the method described in the present invention is sensitive, true and robust.

5. Robustness of the Measurement as a Function of the Cosolvent of $T_2$+HCl

The influence of the organic cosolvent (methanol, ethanol) was tested on polystyrene 96-well microplates coated with amines (Amine™ Corning #2388) which, after conditioning, staining and washing according to the protocol described in Example 1, were destained either with a buffer $T_2$ as described in Example 7, or with a buffer $T_2$ in which the methanol has been replaced with ethanol in the same proportions.

Results

The optical densities measured at 620 nm are:
$T_2$/methanol: 0.151±0.0087 (n=6),
$T_2$/ethanol: 0.147±0.0064 (n=6).

The results obtained with ethanol and methanol are statistically identical (Student's test at 95%). It is therefore possible to replace the methanol with ethanol.

Example 3

Use of the Present Invention for Characterizing Surface Amines on Substrates of Different Format and Material 1. Glass Hemolysis Tube
Format: Hemolysis tube
Materials: Glass
Coating: These tubes were activated according to the method described by Arkas et al. 2005, Metwalli et al. 2006 and Pathak et al. 2004. After activation, the tubes were grafted with third-generation lysine-grafted dendrimers (DGL-G3) (International application WO 2006/114528) using the protocol described by Arkas et al. 2005, Metwalli et al. 2006 and Pathak et al. 2004. After the grafting, the substrates are washed as described above. The grafting of the DGL-G3 was then characterized according to the protocol of the invention described in Example 1, with a staining (step a) and destaining (step b) volume of 3.5 mL.

Results: $OD_{real}$ 0.056±0.08 (n=7), i.e. $3.56 \times 10^{14} NH_2/cm^2$.

2. COC, Polystyrene and Polypropylene Microplates
Format: 24- or 96-well microplates
Materials: COC, polystyrene and polypropylene
Coating: see below
24-well COC plates from Greiner (tailor-made by the supplier) surface-functionalized with epoxides, grafting of DGL-G3 (200 µg/mL in 0.1 M carbonate buffer, pH 9.5) at ambient temperature for 16 h and then washed as described above;
96-well polystyrene, Corning: see Example 1;
96-well polypropylene from Greiner (#655201) activated by argon plasma followed by polymerization of the couple N-acryloyl-N-morpholine and N-acryloyl-N-succinimide (NAM/NAS) in dioxane, washing with water and grafting with DGL-G3 at 1 mg/mL in 0.2 M PBS buffer, pH 7.4. Characterization according to the protocol described in Example 1, after washing of the excess DGL-G3 as described for COC.

Results:

TABLE 2

| Substrate and grafting | $\times 10^{14}$ $NH_2/cm^2$ | |
|---|---|---|
| COC-DGL-$G_3$ | 1.47 ± 17% (n = 24) | |
| Polypropylene-NAM/NAS-DGL-$G_3$ | 4.1 ± 4.6% (n = 47)<br>4.0 ± 4.6% (n = 47) | Staining 1<br>Staining 2 |

With n = number of measurements

The results given in Table 2 show that the coefficients of variation of the graftings on the COC substrates are high and much higher than those obtained on polypropylene. This reveals a problem of homogeneity of the graftings on the COC plate whereas the activation-grafting method used on polypropylene is homogeneous over the entire microplate. Thus, the method described by the present invention makes it possible to study the homogeneity of graftings on a surface.

The method described in the present invention results in staining results that are identical from one cycle to the other (Table 2). Thus, the amines "stained" in the first cycle (staining 1) then "destained" before the second "staining" were all freed and could be "stained" a second time (staining 2) so as to give a result significantly identical to the first measurement. This demonstrates that the present invention 1/makes it possible to verify the stability of the graftings, but also 2/is completely reversible.

Finally, the present invention, which results in the evaluation of the density of the amine functions per unit of surface area ($NH_2/cm^2$), makes it possible to compare, with one another, substrates of different materials, format and grafting.

3. Polypropylene Felts and Disks

Format: 5 mg felts or disks 6 mm in diameter

Materials: Polypropylene

Coating: Identical to the activation method described above for the 96-well polypropylene microplates, grafting with $DGL-G_3$. The characterization is carried out according to the protocol described in Example 1.

Results:

TABLE 3

| Grafting substrate | $\times 10^{14}$ $NH_2$/mg |
|---|---|
| Felts (5 mg) | 1.36 ± 0.08 (CV 5.8%) |
| Disks (3.7 mg-6 mm Ø) | 1.059 ± 0.025 (CV 2.4%) |

With CV: coefficient of variation

All the results given in Example 3 show that the method described in the present invention for detecting and quantifying the surface amines of a solid substrate is quantitative, reversible, and suitable for many materials, formats and coatings as described above. The method described makes it possible to verify the homogeneity and the stability of the graftings.

Example 4

Use of the Present Invention for Characterizing the Instability of the Grafting of Proteins Adsorbed onto Solid Substrates Format: 24- and 96-well microplates Materials: Polystyrene (Greiner and Nunc)

Coating:

Greiner: Cellcoated© poly-L-lysine (ref 655930) 96-well and 24-well format made on demand by the supplier according to the "Cellcoated© poly-L-lysine" protocol;

Nunc: Microwell poly-D-lysine reference: 152039.

Results:

TABLE 4

| Grafting substrate | Staining 1 $\times 10^{14}$ $NH_2/cm^2$ | Staining 2 $\times 10^{14}$ $NH_2/cm^2$ |
|---|---|---|
| Greiner-PLL 96-well | 0.514 (CV 11%, n = 96) | BN |
| Greiner-PLL 24-well | 1.471 (CV 14%, n = 24) | 0.927 (CV14%, n = 24) |
| NUNC-PDL 96-well | 0.232 (CV 27%, n = 96) | LOD < OD < LOQ | with PLL = poly-L-lysine,
PDL = poly-D-lysine,
BN = background noise,
CV = coefficient of variation,
LOD = limit of detection,
LOQ = limit of quantification The results in Table 4 show that the method described in the present patent makes it possible to demonstrate the nonhomogeneity of the graftings (in this case by adsorption) and also the instability of the grafting when the proteins are adsorbed and not covalently grafted onto the support.

Example 5

Reproducibility of Indirect Graftings Using Glutaraldehyde

The immobilization of the DGL (generation G3) dendrimeric interface was carried out via a homobifunctional link (glutaraldehyde) on a substrate surface-functionalized with amines (NHR, Covalink™). The protocol is commonly used in the laboratory for binding histamine [Claeys-Bruno, 2006]. The volume of solution is 200 μL/well. The results obtained are given in Table 4 below.

TABLE 5

| Concentration introduced | Concentration of blue (μg/mL) |
|---|---|
| Without DGL "NHR commercial substrate" | 0.16 ± 0.01 |
| 100 μg/well | 5.0 ± 0.3 |
| 200 μg/well | 6.0 ± 1.0 |
| 400 μg/well | 5.1 ± 0.7 |
| 1000 μg/well | 5.3 ± 0.8 |

This work made it possible, firstly, to set up the optimum washing conditions for maximum removal of the possible DGL aggregates and the nonspecific adsorptions on the substrate. The values given in Table 5 are obtained after 3 carbonate buffer/50% MeOH washing baths. Similarly, after 6 staining/destaining cycles on these coated substrates, the value of the Coomassie blue in $T_2$ does not vary per well, the blue values being identical at the 95% threshold for the same well after staining/destaining cycles.

Secondly, by virtue of the present invention, it was demonstrated that a concentration of less than 100 μg of DGL (G3) is sufficient for the formation of a coated substrate in the case of the strategy using glutaraldehyde as bifunctional agent.

However, the present strategy also made it possible to demonstrate that a great variability exists in terms of the values obtained on graftings carried out on two different days and sometimes even from one well to the other with this strategy of grafting using glutaraldehyde as bifunctional agent. It could therefore be verified in this particular case that a strategy of immobilization using the glutaraldehyde link does not result in grafting homogeneity. The substrates thus coated do not therefore meet the criterion of reproducibility.

Whatever the DGL concentration introduced, the coated substrates result in Coomassie blue concentrations over 30 times higher than those of the commercial substrate. In addition, DGL graftings by adsorption onto the substrate show that, after washes in carbonate buffer/MeOH baths, the blue values obtained in $T_2$ are not significantly different from those obtained on the NHR substrate. This suggests that:

1/ the nonspecific adsorptions have indeed been eliminated;

2/ the values read correlate only with DGLs covalently grafted to the support;

3/ the strategy of immobilization of the DGL interface via glutaraldehyde nevertheless makes it possible to obtain surface-amine densities that are much higher than the previous strategy, and compared with the commercial substrate, since there are approximately $8 \times 10^{14}$ molecules of blue per well after the destaining step (gain in sensitivity).

Example 6

Use of the Present Invention for Characterizing Various Proteins Immobilized on a Solid Substrate (Synthetic Dendrimers, Synthetic and Natural Proteins, Antibodies)

Format: 96-well microplates
Materials: Polystyrene
Coating: Plates surface-functionalized with epoxides (Nunc, immobilizer NH₂™). The proteins are grafted at 200 µg/mL in the 0.1 M carbonate buffer, pH 9, except for the antibodies, which are grafted in the 0.2 M PBS buffer, pH 7.4, as described for the polypropylene plates in Example 3.

TABLE 6

| Proteins | Molecular mass Dalton |
|---|---|
| Lysine-grafted dendrimers (WO 2006/114528) | |
| G2 | 8 350 |
| G3 | 21 500 |
| G4 | 64 000 |
| G5 | 169 000 |
| Linear polylysine-Sigma | 15-30 000 |
| PAMAM G5 (Sigma) | 28 825 |
| Lysozyme (Fluka) | 16 000 |
| Bovine serum albumin (BSA) | 69 000 |
| Monoclonal antibodies (Pierce # 0031242) | 150 000 |

Figure 4:
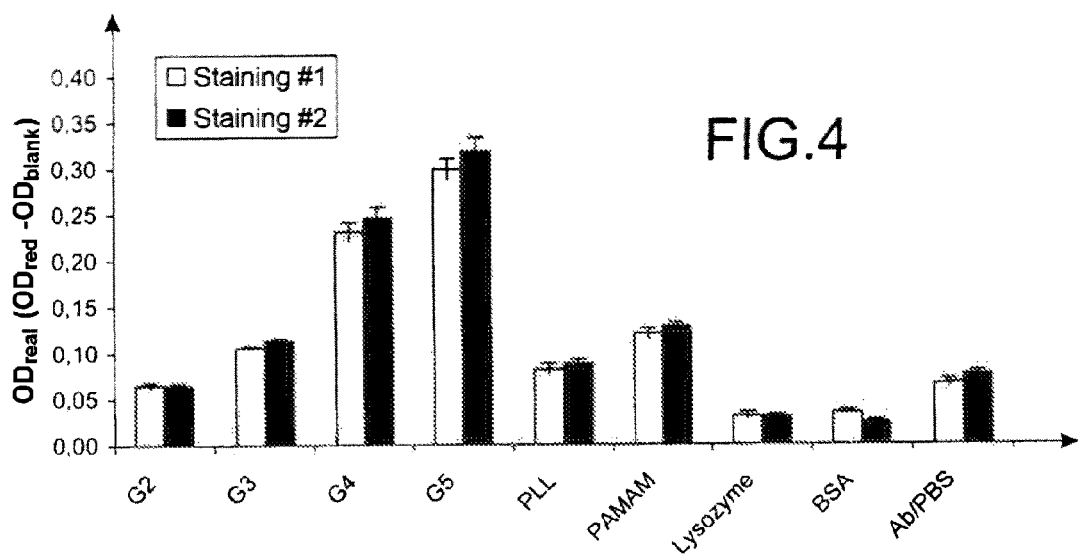
FIG. 4 shows the real absorbance of Coomassie blue in the solution $T_2$/HCl, measured after a single staining/destaining cycle (staining 1) or after two staining/destaining cycles (staining 2), for various molecules immobilized on a polystyrene solid substrate, which are $2^{nd}$-generation (G2), $3^{rd}$-generation (G3), $4^{th}$-generation (G4) and $5^{th}$-generation (G5) lysine-grafted dendrimers (international application WO 2006/114528); polyamidoamine (PAMAM) dendrimers; natural proteins (bovine serum albumin (BSA) and lysozyme); synthetic proteins (linear polylysine (PLL)) and monoclonal antibodies (Ab/PBS).

RESULTS: FIG. 4 shows that the method described makes it possible equally to characterize surface amines derived from natural proteins and those which are synthetic in a repeatable manner. Thus, the method can be used on proteins of variable mass and origin (natural, synthetic) and also on synthetic amines (see Example 1).

LITERATURE REFERENCES

Arkas M., Tsiourvas D Paleos C. M. (2005). "Organosilicon Dendritic Networks in Porous Ceramics for Water Purification." Chemistry of Material, 17: 3439-44.

Atherton, B. A., E. L. Cunningham and A. G. Splittgerber (1996). "A mathematical model for the description of the coomassie brilliant blue protein assay." Analytical Biochemistry 233: 160-168.

Bradford, M. M. (1976). "A rapid and sensitive method for the quantitation of microgram quantities of protein utilizing the principle of protein-dye binding." Analytical Biochemistry 72: 248-254.

Chial, H. J., H. B. Thompson, et al. (1993). "A spectral study of the charge forms of Coomassie blue G." Analytical Biochemistry 209(2): 258-266.

Chial, H. J. and A. G. Splittgerber (1993). "A comparison of the binding of Coomassie brilliant blue to proteins at low and neutral pH." Analytical Biochemistry 213(2): 362-369.

Congdon, R. W., G. W. Muth, et al. (1993). "The binding interaction of Coomassie blue with proteins." Analytical Biochemistry 213(2): 407-413.

Claeys-Bruno, M., O. Vandenabeele-Trambouze, et al. (2006). "Methodological approaches for histamine quantification using derivatization by chloroethylnitrosourea and ELISA measurement. Part I. Optimization of derivated histamine detection with coated-plates using optimal design and Part II: Optimisation of the derivatization step." Chemometrics and Intelligent Laboratory Systems 80(2): 176-197.

Metwalli E., Haines D. Becker O., Conzone S., Pantano C. G. (2006) "Surface characterizations of mono-, di-, and tri-aminosilane treated glass substrates." Journal of Colloid and Interface Science, 298: 8252-31.

Pathak S. Singh A. K., McElhanon J. R., Dentinger P. M. (2004) "Dendrimer-activated surfaces for high density and high activity protein chip applications" Langmuir, 20: 6075-79.

U.S. Pat. No. 6,696,304 (Luminex corporation) published on 24 Feb. 2004.

U.S. Pat. No. 6,555,382 (Wondrak E. M.) published on 29 Nov. 2001.

International application WO 2006/114528 (CNRS & UNIVERSITE MONTPELLIER II) published on 2 Nov. 2006.

The invention claimed is:

1. A method for detecting at least one molecule comprising at least one protonated nitrogen group immobilized at the surface of a solid substrate and for determining the number of protonated nitrogen groups at said surface, said method comprising the following successive steps:

a) bringing said surface of the solid substrate onto which at least one molecule comprising at least one protonated nitrogen group is immobilized, into contact with a solution $T_1$ containing a coloring agent having properties of absorption, emission or reemission in a wavelength range of from 280 to 3000 nm, wherein said coloring agent is capable of reacting with said molecule comprising at least one protonated nitrogen group, wherein said coloring agent is Coomassie blue G250, b) removing said coloring agent which has not reacted with said surface during step (a), c) bringing said surface into contact with a solution $T_2$ capable of dissociating the complex formed between said coloring agent and said molecule comprising at least one protonated nitrogen group thereby the coloring returns to solution in solution $T_2$, wherein said solution $T_2$ is an aqueous solution containing an alcohol and carbonate ions, wherein the pH of said solution $T_2$ is greater than 11, and wherein the proportion of alcohol is between 40% and 60% by volume, relative to the total volume of solution $T_2$, d) acidifying said solution $T_2$ and detecting said coloring agent present in the acidified solution $T_2$ so as to detect said molecule comprising at least one protonated nitrogen group and to determine the number of protonated nitrogen groups at the surface of said solid substrate.

2. The method as claimed in claim 1, wherein said solid substrate or at least said surface of said solid substrate where said molecule comprising at least one protonated nitrogen group is immobilized, is an inorganic solid substrate or surface.

3. The method as claimed in claim 1, wherein said solid substrate or at least said surface of said solid substrate where said molecule comprising at least one protonated nitrogen group is immobilized, is made of an organic material.

4. The method as claimed in claim 1, wherein said solid substrate has a surface bearing functional groups by means of which said molecule comprising at least one protonated nitrogen group is capable of being immobilized.

5. The method as claimed in claim 1, wherein said molecule comprising at least one protonated nitrogen group is immobilized indirectly at the surface of the solid substrate.

6. The method as claimed in claim 1, wherein said solution $T_1$ is an aqueous solution comprising an alcohol and/or an acid, the pH of said solution $T_1$ being greater than 1.

7. The method as claimed in claim 6, wherein said alcohol is selected from the group consisting of methanol, ethanol, propanol, isopropanol, butanol and mixtures thereof, the proportion of alcohol being between 1% and 25% by volume, relative to the total volume of solution $T_1$.

8. The method as claimed in claim 6, wherein said acid is selected from the group consisting of acetic acid, trichloroacetic acid and mixtures thereof, the proportion of acid being between 0.5% and 20% by volume, relative to the total volume of solution $T_1$.

9. The method as claimed in claim 7, wherein said acid is selected from the group consisting of acetic acid, trichloroacetic acid and mixtures thereof, the proportion of acid being between 0.5% and 20% by volume, relative to the total volume of solution $T_1$.

10. The method as claimed in claim 1, wherein said coloring agent is used in an amount of between 0.001% and 1% by mass, relative to the total volume of solution $T_1$.

11. The method as claimed in claim 1, wherein said step (b) comprises at least one wash of the surface of the solid substrate by means of identical or different washing solutions.

12. The method as claimed in claim 11, wherein said washing solutions are selected from the group consisting of water, distilled water, demineralized water, deionized water, a phosphate buffered saline, a saline solution, an acetate buffer, a carbonate buffer, an aqueous solution comprising an alcohol and/or an acid as defined in claims 8 to 10, and mixtures thereof.

13. The method as claimed in claim 1, wherein said alcohol is selected from the group-consisting of methanol, ethanol, propanol, isopropanol, butanol and mixtures thereof.

14. The method as claimed in claim 1, wherein said carbonate ions in the solution $T_2$ have a molarity of between 0.001 and 1 M.

15. The method as claimed in claim 1, wherein said detection of the coloring agent during step (d) consists in measuring an optical density of the acidified solution $T_2$ obtained after step (c).

16. Method for comparing various strategies for immobilizing molecules comprising at least one protonated nitrogen group on solid substrates and capable of generating coated substrates, peptide chips, protein chips, antibody chips or cell chips consisting in applying a method as defined in claim 1 on said coated substrates, peptide chips, protein chips, antibody chips or cell chips.

17. Method for verifying the robustness, the stability and the sensitivity of the coated substrates, of the peptide chips, of the protein chips, of the antibody chips or of the cell chips consisting in applying a method as defined in claim 1 on said coated substrates, peptide chips, protein chips, antibody chips or cell chips.

18. Method for detecting and optionally quantifying at least one protein, at least one antibody or at least one of their fragments present in a liquid of interest consisting in preparing a solid substrate having, at its surface, at least one antigen or at least one antibody specific for the protein, for the antibody or for their fragments being sought, bringing the substrate thus prepared into contact with the liquid of interest, applying a method as defined in claim 1.

19. The method as claimed in claim 1, wherein said protonated nitrogen group is selected from the group consisting of a primary amine function of formula —$NH_2$, a secondary amine function of formula —NHR, R representing a carbon-based group, a tertiary amine function of formula —NR'R, R and R' representing identical or different carbon-based groups, or belonging to the same carbon-based group, an imine function, a guanidino function and a heteroaryl group.

* * * * *